United States Patent [19]
Horigome et al.

[11] Patent Number: 5,309,765
[45] Date of Patent: May 10, 1994

[54] METHOD AND APPARATUS FOR PERFORMING ULTRASONIC FLAW DETECTION BY CONTROLLING PEAK FREQUENCY AND FREQUENCY BANDWIDTH

[75] Inventors: Hidekazu Horigome; Hideya Tanabe; Katsuyuki Nishifuji, all of Tokyo, Japan

[73] Assignee: NKK Corporation, Tokyo, Japan

[21] Appl. No.: 790,471

[22] Filed: Nov. 12, 1991

[30] Foreign Application Priority Data

Nov. 14, 1990 [JP] Japan ................................ 2-309901
Jul. 1, 1991 [JP] Japan ................................ 3-160676

[51] Int. Cl.$^5$ ............................................. G01N 29/10
[52] U.S. Cl. ............................... 73/602; 73/614; 73/620
[58] Field of Search ................. 73/602, 614, 620, 629, 73/630

[56] References Cited

U.S. PATENT DOCUMENTS

| | | |
|---|---|---|
| 4,052,889 | 10/1977 | Mucciardi et al. . |
| 4,364,273 | 12/1982 | Redding .......................... 73/614 |
| 4,545,250 | 10/1985 | Miwa .............................. 73/602 |
| 4,603,584 | 8/1986 | Bartle et al. ...................... 73/602 |
| 4,759,221 | 7/1988 | Ortlieb et al. . |

FOREIGN PATENT DOCUMENTS

| | | |
|---|---|---|
| 0119844 | 9/1984 | European Pat. Off. . |
| 0191346 | 8/1986 | European Pat. Off. . |
| 0284678 | 10/1988 | European Pat. Off. . |
| 59-10501 | 3/1984 | Japan . |
| 62-54160 | 3/1987 | Japan . |
| 62-180267 | 8/1987 | Japan . |
| 2143036 | 1/1985 | United Kingdom . |

*Primary Examiner*—Hezron E. Williams
*Assistant Examiner*—Rose Finley
*Attorney, Agent, or Firm*—Frishauf, Holtz, Goodman & Woodward

[57] ABSTRACT

An apparatus for performing ultrasonic flaw detection, wherein an ultrasonic transmitter transmits a pulse signal having a designated carrier frequency and a designated cycle count to an ultrasonic probe. An ultrasonic receiver receives the echo signal output from the ultrasonic probe. The peak frequency and the frequency bandwidth of the echo signal received by the ultrasonic receiving unit are detected by a signal analysis unit. A transmission control unit designates the carrier frequency and the cycle count of the pulse signal output from the ultrasonic transmission unit so that the detected peak frequency and the detected frequency bandwidth become a flaw detection condition peak frequency and a flaw detection condition frequency bandwidth, respectively.

12 Claims, 11 Drawing Sheets

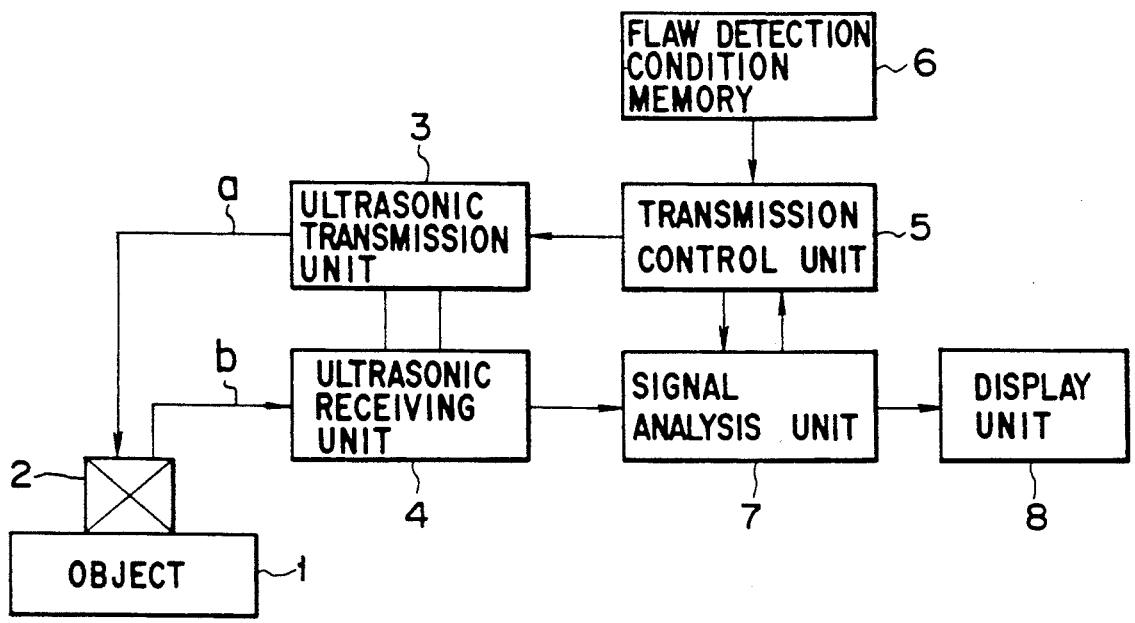
FIG. 1
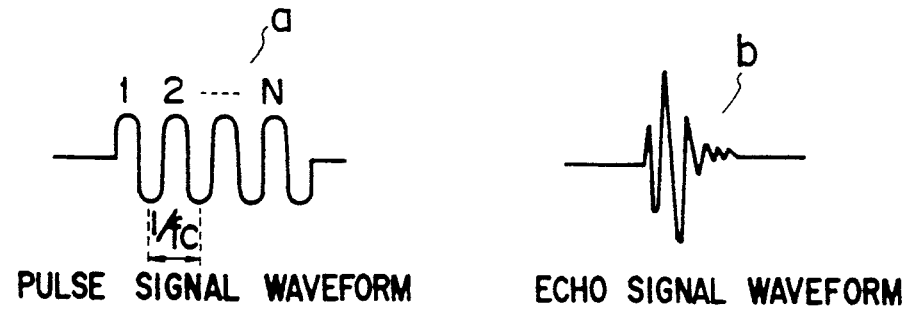
FIG. 2A — PULSE SIGNAL WAVEFORM
FIG. 2B — ECHO SIGNAL WAVEFORM
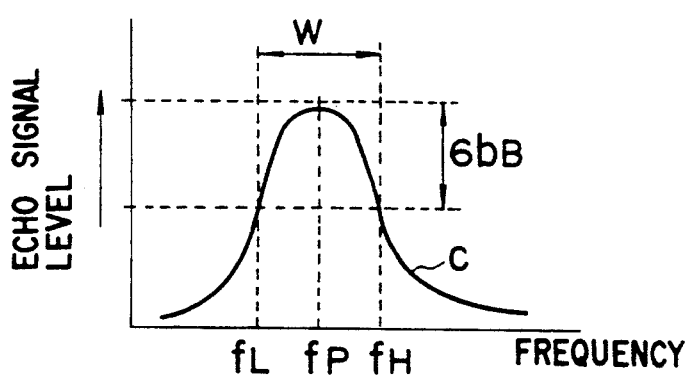
ECHO SIGNAL FREQUENCY CHARACTERISTICS
FIG. 2C

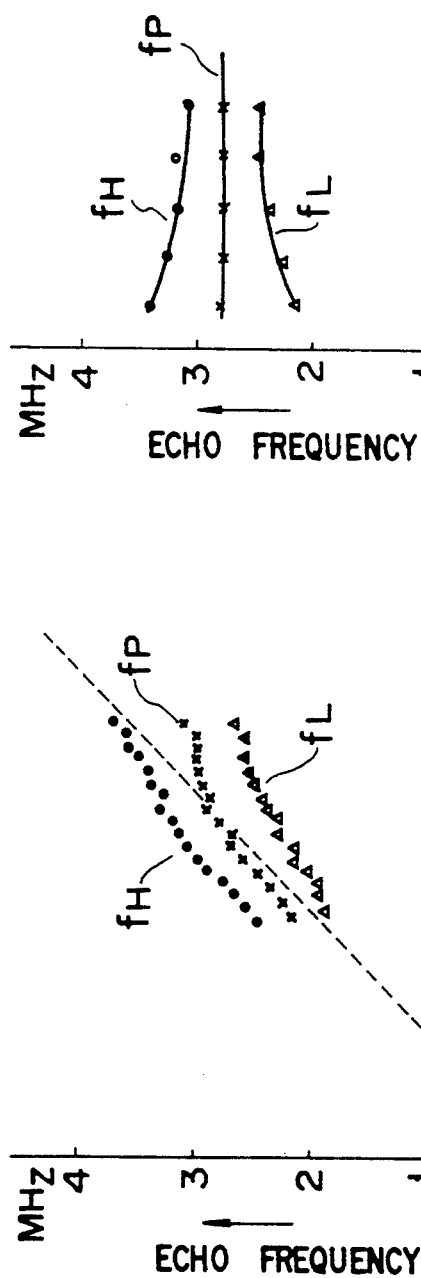
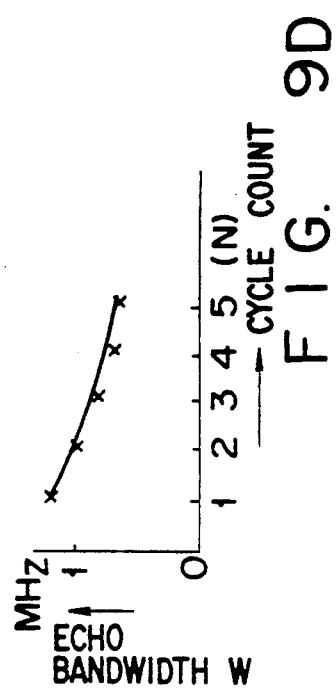
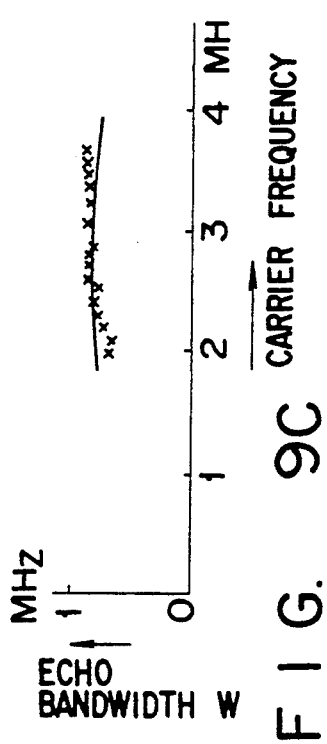
FIG. 9A
FIG. 9B
FIG. 9C
FIG. 9D

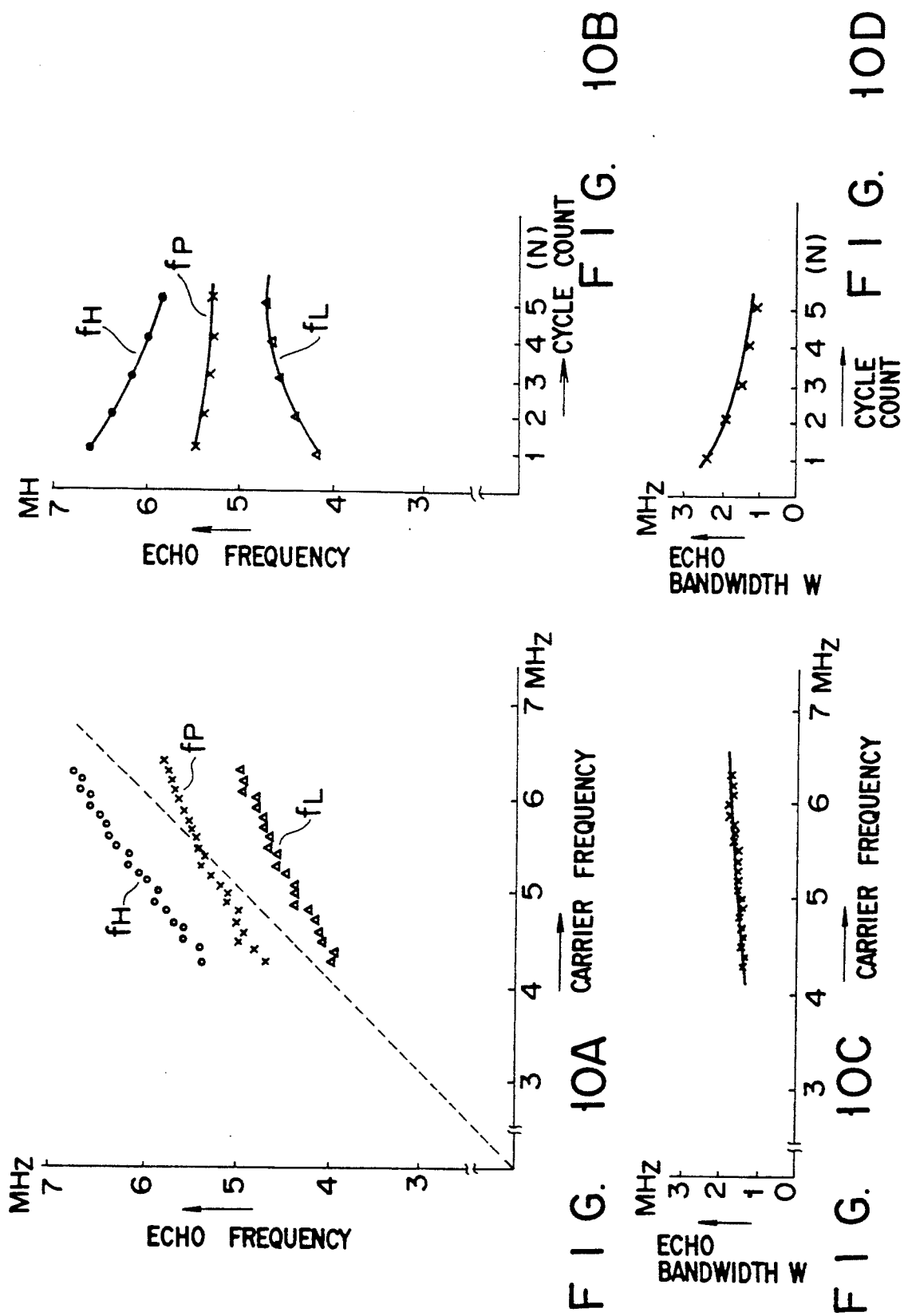

ined by physical conditions such as a material of
a test object, and finally, to provide a method and apparatus for performing ultrasonic flaw detection capable of performing sensitivity adjustment between channels

METHOD AND APPARATUS FOR PERFORMING ULTRASONIC FLAW DETECTION BY CONTROLLING PEAK FREQUENCY AND FREQUENCY BANDWIDTH

BACKGROUND OF THE INVENTION

1. Field of the Invention

The present invention relates to an ultrasonic flaw detection method for detecting a defect present in a test object by using an ultrasonic probe, and an ultrasonic flaw detection apparatus employing this method and, more particularly, to a method and apparatus for performing ultrasonic flaw detection, in which a peak frequency and a frequency bandwidth of an echo signal obtained from the ultrasonic probe attached to the object are independently controlled.

2. Description of the Related Art

In an ultrasonic flaw detection apparatus for detecting defects or flaws present on the surface of or inside a steel plate by using an ultrasonic wave, an impulse signal obtained by utilizing discharge characteristics or the like of, e.g., a charge circuit is applied to an ultrasonic probe attached to the surface of the object. An ultrasonic wave is transmitted from the ultrasonic probe to the inside of the object. When a defect is present, upon propagation of the ultrasonic wave inside the object, a reflected wave is generated. The ultrasonic probe detects this reflected wave and outputs it as an echo signal. The level of the echo signal output from the ultrasonic probe corresponds to the size and shape of the defect. Therefore, the presence/absence of the defect and its size and shape are detected in accordance with this signal level.

In this conventional apparatus, eve if flaw detectors having the same technical specifications and ultrasonic probes having the same technical specifications are used, and even if the same defect is detected by these components, if a plurality of channels are present, the same results cannot be expected between the channels due to the following reason. The properties of an object are not always uniform, and ultrasonic probes do not necessarily have identical characteristics. For these reasons, differences occur between the characteristics of the channels. As a result, frequency characteristics such as operating frequencies and frequency bands of the respective channels are fixed to different values.

A wide-band probe has advantages in that the echo width of a received echo signal is sharp, and that an S/N ratio obtained with an attenuating material is higher than that of a narrow-band probe. Since the electrical impedance of this wide-band probe, however, is low, the differences in characteristics have large influences on output waveforms. Variations in frequency characteristics such as operating frequency characteristics and frequency bandwidths therefore occur between the respective probes. In a multichannel ultrasonic flaw detection apparatus having a probe array consisting of a plurality of ultrasonic probes, it is impossible to obtain a uniform flaw detection sensitivity of the object as a whole.

In addition, when an ultrasonic probe is replaced with a new one, differences in characteristics between the ultrasonic probes are present. For this reason, adjustment must be performed in accordance with these differences in characteristics and deterioration over time in each ultrasonic probe. The adjustment operations are time-consuming and cumbersome and require much labor.

An ultrasonic flaw detection method called a CS method (Controlled Signal Technique) is proposed in which an impulse signal is not applied to an ultrasonic probe. According to this CS method, as shown in FIG. 11A, a tone-burst pulse signal obtained by extracting a carrier wave having a predetermined carrier frequency $f_c$ every predetermined time interval is applied to the ultrasonic probe. Some techniques of the CS method are introduced in Published Unexamined Japanese patent Application Nos. 62-180267 and 62-54160 and Published Examined Japanese Patent Application No. 59-10501.

The tone-burst pulse signal has frequency characteristics as shown in FIG. 11B. Frequency components in a narrow band centered on a peak frequency $f_P$ are present, as shown in FIG. 12. For the sake of comparison, a characteristic curve indicated by a dotted line is a frequency characteristic curve obtained when an impulse signal is applied. When the carrier frequency $f_c$ of the impulse signal to be applied to the ultrasonic probe is changed, the peak frequency $f_P$ of the echo signal changes accordingly. For example, when the carrier frequency $f_c$ of the pulse signal is changed in an order of 3, 3.5, 4, 4.5, 5, 5.5, 6, 6.5, and 7 MHz, the peak frequency $f_P$ of the echo signal changes in an order of 3, 3.5, 4, 4.5, 5, 5.5, 6, 6.5, and 7 MHz accordingly, as shown in FIG. 13.

As the cycle count N representing the number of waves included in the pulse signal is increased, the ratio of the components of the carrier frequency $f_c$ to other frequency components of the pulse signal is increased. As a result, the bandwidth of the pulse signal is narrowed, and a steep frequency characteristic curve is obtained. FIG. 14A shows a pulse signal waveform for $N=1$. FIG. 14B shows a frequency characteristic curve of the pulse signal shown in FIG. 14A. FIGS. 15A and 15B show a signal waveform and frequency characteristics for $N=5$. FIGS. 16A and 16B show a signal waveform and frequency characteristics for $N=10$.

It is thus understood that the bandwidth of the pulse signal is decreased with an increase in cycle count N of the pulse signal. When the cycle count N is changed, the frequency bandwidth W of the ultrasonic waves applied to the object can be changed to an arbitrary value.

In practice, a uniform flaw detection sensitivity in the entire detection range of an object in a multichannel ultrasonic flaw detection apparatus having an array of a plurality of ultrasonic probes must be realized. At the same time, adjustment operations based on the differences in characteristics upon replacement of a probe and the deterioration over time in each probe must be performed. It is very difficult to control that the frequency characteristics such as the peak frequency $f_P$ and the frequency bandwidth W of the echo signal output from the ultrasonic probe satisfy the above conditions.

SUMMARY OF THE INVENTION

It is an object of the present invention to independently control parameters of echo signal frequency characteristics matching with flaw detection conditions determined by physical conditions such as a material of a test object, and finally, to provide a method and apparatus for performing ultrasonic flaw detection capable of performing sensitivity adjustment between channels and greatly improving flaw detection accuracy even in a multichannel ultrasonic flaw detection apparatus.

In order to achieve the above object, according to an ultrasonic flaw detection method of the present invention, a pulse signal is transmitted to an ultrasonic probe attached to the object to cause an ultrasonic wave to be incident on the object, and a reflected wave of the ultrasonic wave incident on the object is received by the ultrasonic probe, thereby obtaining an echo signal. A carrier frequency of the pulse signal is set so that the peak frequency of the echo signal is set to be a predetermined frequency, and the cycle count of the pulse signal is determined so that the frequency bandwidth of the echo signal is set to be a predetermined bandwidth. A defect present in the object is detected in accordance with the signal level of the echo signal output from the ultrasonic probe.

According to experimental results, even if the carrier frequency of the pulse signal is changed, the frequency bandwidth of the echo signal is almost not changed. At the same time, even if the cycle count of the pulse signal is changed, the peak frequency f of the echo signal is almost not changed. In consideration of this, the peak frequency of the echo signal is controlled by only the carrier frequency of the pulse signal, and the frequency bandwidth of the echo signal is controlled by only the cycle count of the pulse signal. Therefore, the peak frequency and the frequency bandwidth of the echo signal can be independently controlled.

In order to achieve the above object according to the present invention there is provided an ultrasonic flaw detection apparatus comprising an ultrasonic wave transmission unit for outputting a pulse signal having a designated carrier frequency and a designated cycle count, an ultrasonic probe, attached to a test object, for outputting an ultrasonic wave to the object in response to the pulse signal input from the ultrasonic transmission unit and for outputting an echo signal upon reception of a reflected wave of the ultrasonic wave, an ultrasonic wave reception unit for receiving the echo signal output from the ultrasonic probe, a signal analysis unit for detecting a peak frequency and a low-frequency bandwidth of the echo signal received by the ultrasonic reception unit, and a transmission control unit for designating the carrier frequency and the cycle count of the pulse signal output from the ultrasonic wave transmission unit so that the peak frequency and the frequency bandwidth which are detected by the signal analysis unit are set to be an optimal peak frequency and an optimal frequency bandwidth, respectively.

The peak frequency and the frequency bandwidth of the echo signal output from the ultrasonic probe can b controlled to an optimal peak frequency and an optimal frequency bandwidth which are determined by, e.g., the material of a test object of interest. As a result, the flaw detection for the object ca be performed in optimal flaw detection conditions.

BRIEF DESCRIPTION OF THE DRAWINGS

FIG. 1 is a block diagram showing a schematic arrangement of an ultrasonic flaw detection apparatus employing an ultrasonic flaw detection method according to an embodiment of the present invention;

FIG. 2A is a waveform chart showing a pulse signal in the apparatus shown in FIG. 1;

FIG. 2B is a waveform chart showing an echo signal in the apparatus shown in FIG. 1;

FIG. 2C is a graph showing frequency characteristics of the echo signal in the apparatus shown in FIG. 1;

FIG. 9A is a graph showing the echo frequency and echo bandwidth as a function of the carrier frequency;

FIG. 9B is a graph showing the echo frequency and echo bandwidth as a function of the cycle count;

FIG. 9C is a graph showing the echo frequency and echo bandwidth as a function of the carrier frequency;

FIG. 9D is a graph showing the echo frequency and echo bandwidth as a function of the cycle count;

FIG. 10A is a graph showing the echo frequency and echo bandwidth as a function of the carrier frequency;

FIG. 10B is a graph showing the echo frequency and echo bandwidth as a function of the cycle count;

FIG. 10C is a graph showing the echo frequency and echo bandwidth as a function of the carrier frequency;

FIG. 10D is a graph showing the echo frequency and echo bandwidth as a function of the cycle count;

DETAILED DESCRIPTION OF THE PREFERRED EMBODIMENTS

Figure 3:
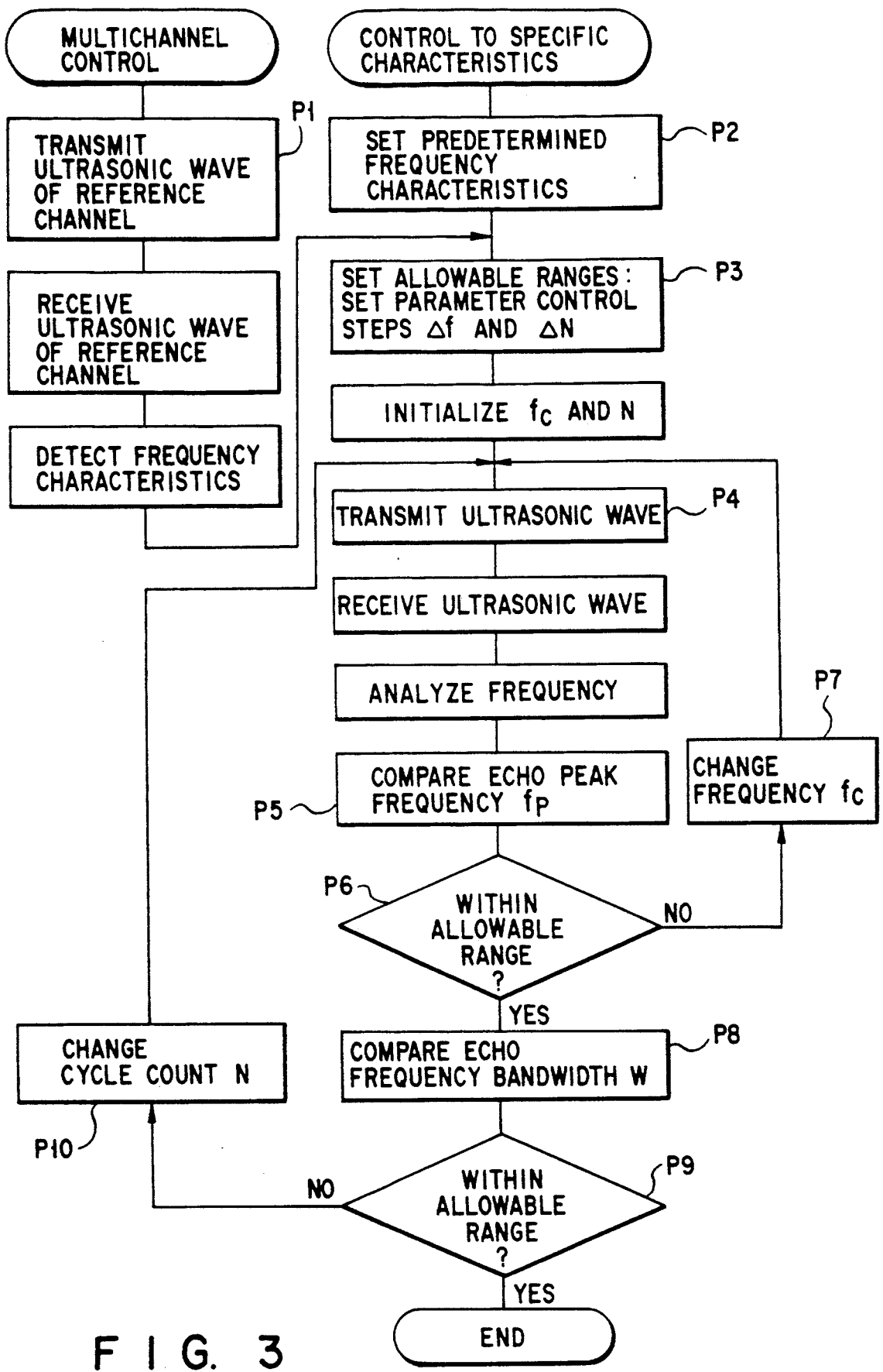
FIG. 3 is a flow chart showing an operation of the ultrasonic flaw detection apparatus shown in FIG. 1.

A description will be made on the basis of experimental results so as to prove that a peak frequency $f_p$ and a frequency bandwidth W of an echo signal output from an ultrasonic probe can be independently controlled.

For example, when a tone-burst pulse signal a having the carrier frequency $f_c$ and the cycle count N, as shown in FIG. 2A, is applied to an ultrasonic probe attached to the surface of a test object, an ultrasonic wave is incident from the ultrasonic probe onto the object. If a defect is present in the object, this ultrasonic wave is reflected by this defect, and a reflected wave is incident on the ultrasonic probe. As a result, an echo signal b having a waveform shown in FIG. 2B is output from the ultrasonic probe.

The frequency of this echo signal b is analyzed to obtain a frequency characteristic curve c shown in FIG. 2C. The frequency at the maximum signal level of this frequency characteristic curve c is defined as the peak frequency $f_P$. Frequencies at levels 6 dB below the maximum signal level of the frequency characteristic curve c are defined as −6-dB lower frequencies $f_H$ and $f_L$. A width at a position 6 dB below the maximum signal level of the frequency characteristic curve c is defined as a frequency bandwidth W $(=f_H−f_L)$.

Experimental values showing changes in characteristic values $f_P$, $f_H$, $f_L$, and W of the echo signal b output from one ultrasonic probe A, which values are obtained by independently changing the carrier frequency $f_c$ and the cycle count N of the pulse signal a applied to the ultrasonic probe A, are shown in FIGS. 9A to 9D.

FIG. 9A is a graph showing changes in the peak frequency $f_P$ and the −6-dB lower frequencies $f_H$ and $f_L$ when the cycle count N is fixed and the carrier frequency $f_c$ is changed within the range of 2 to 4 MHz. FIG. 9C is a graph showing changes in the frequency bandwidth W when the cycle count N is fixed and the carrier frequency $f_c$ is changed in the range of 2 to 4 MHz.

FIG. 9B is a graph showing changes in the peak frequency $f_P$ and the −6-dB lower frequencies $f_H$ and $f_L$ when the carrier frequency $f_c$ is fixed and the cycle count N is changed in the range of 1 to 5. FIG. 9D is a graph showing changes in the frequency bandwidth W when the carrier frequency $f_c$ is fixed and the cycle count N is changed in the range of 1 to 5.

As is apparent from the experimental results shown in FIGS. 9A to 9D, even if the carrier frequency $f_c$ of the pulse signal a is changed, the frequency bandwidth W of the echo signal b is almost not changed. Even if the cycle count N of the pulse signal a is changed, the peak frequency $f_P$ of the echo signal b is almost not changed. That is, the peak frequency $f_P$ of the echo signal b is changed by only the carrier frequency $f_c$ of the pulse signal a. The frequency bandwidth W of the echo signal b is controlled by only the cycle count N of the pulse signal a. Therefore, the peak frequency $f_P$ and the frequency bandwidth W of the echo signal b can be independently controlled.

In the ultrasonic probe A shown in the experiment of FIGS. 9A to 9D, even if the cycle count N is changed, the peak frequency $f_P$ is almost not changed. When the frequency bandwidth W is adjusted to a target frequency bandwidth after the peak frequency $f_P$ is adjusted to a target frequency, flaw detection conditions for the object can be set by a single operation.

Experimental results obtained using an ultrasonic probe B having different specifications from those of the ultrasonic probe A shown in FIGS. 9A to 9D are shown in FIGS. 10A to 10D. That is, FIGS. 10A to 10D show changes in respective characteristic values $f_P$, $f_H$, $f_L$, and W of an echo signal b output from the ultrasonic probe B when a carrier frequency $f_c$ and the cycle count N of the pulse signal a applied to the ultrasonic probe B are independently changed. Note that the carrier frequency $f_c$ of the pulse signal a is set slightly higher than that applied to the ultrasonic probe A, and other conditions are the same as those in the ultrasonic probe A.

As is apparent from the experimental results shown in FIGS. 10A to 10D, the peak frequency $f_P$ and the frequency bandwidth W of the echo signal b are independently controlled. In FIGS. 10A to 10D, when the cycle count N is changed, the peak frequency $f_P$ is slightly changed, so that a plurality of adjustment operations are required to obtain target frequency characteristics. As shown in FIG. 10B, however, since the degree of change in peak frequency $f_P$ is very small, adjustment need only be repeated a maximum of several times.

When the carrier frequency $f_c$ and the cycle count N of the pulse signal a applied to the ultrasonic probe are changed, the peak frequency $f_P$ and the frequency bandwidth W of the echo signal b obtained upon detection of a defect by the ultrasonic probe can be independently controlled. The frequency characteristics of the echo signal b can be easily matched with optimal flaw detection conditions, thereby greatly improving flaw detection precision.

There are provided a technique for matching the frequency bandwidth W with an optimal frequency bandwidth determined by the material of an object after the peak frequency $f_P$ of the echo signal b is matched with an optimal frequency determined by the material of the object, and a technique for matching the peak frequency with an optimal value after the frequency bandwidth is matched with an optimal value. In either technique, the target peak frequency and frequency bandwidth can be obtained.

Control of the peak frequency can be performed independently of control of the frequency bandwidth.

FIG. 1 is a block diagram showing a schematic arrangement of an ultrasonic flaw detection apparatus employing a flaw detection method of this embodiment.

An object 1 is a steel plate or the like. For example, a vertical ultrasonic probe 2 is attached to the surface of the object 1. The tone-burst signal a having the carrier frequency $f_c$ and the cycle count N, as shown in FIG. 2A, is applied from an ultrasonic transmission unit 3 to the ultrasonic probe 2. If a defect or flaw is present in the object 1, the echo signal b shown in FIG. 2B is output from the ultrasonic probe 2 to an ultrasonic receiving unit 4.

A transmission control unit 5 comprises, e.g., a microcomputer. The transmission control unit 5 controls the carrier frequency $f_c$ and the cycle count N of the pulse signal a output from the ultrasonic transmission unit 3 in accordance with flaw detection conditions stored in a flaw detection condition memory 6. A signal analysis unit 7 has, e.g., an FFT (Fast-Fourier Transform) function and analyzes the frequency of the echo signal b received by the ultrasonic receiving unit 4 and feeds back the analysis result to the transmission control unit 5. The signal analysis unit 7 also determines the presence/absence of a defect in accordance with the level of the input echo signal b. In addition, the signal analysis unit 7 can also calculate the size of a defect and display it on a display unit 8.

The flaw detection condition memory 6 stores, in units of materials of the objects 1, the optimal peak frequency $f_P$ and the optimal frequency bandwidth W of the echo signal b output from the ultrasonic probe 2 attached to the object 1. Various conditions such as allowable ranges Δfm and ΔWm of the peak frequency $f_P$ and the frequency bandwidth W are also stored in the flaw detection condition memory 6.

When a flaw detection condition command is input from a keyboard (not shown) to the transmission control unit 5, the carrier frequency $f_c$ and the cycle count N of the pulse signal a are set in accordance with a flow chart in FIG. 3.

If this ultrasonic flaw detection apparatus is a multichannel apparatus, a large number of probes 2 are regarded to be arranged on one object 1. Peak frequencies $f_P$ and frequency bandwidths W of echo signals b obtained from all channels except for a reference channel must be matched with those of the reference channel.

In this case, in step P (program step) 1, the transmission control unit 5 transmits a transmission command to the ultrasonic transmission unit 3 of the reference channel to cause the ultrasonic transmission unit 3 to output a pulse signal a having a carrier frequency $f_c$ and a cycle count N which are currently set in the ultrasonic transmission unit 3. The ultrasonic receiving unit 4 receives the echo signal b output from the ultrasonic probe 2. The signal analysis unit 7 performs frequency analysis of the received echo signal to obtain the peak frequency $f_P$, the $-6$-dB lower frequencies $f_H$ and $f_L$, and the frequency bandwidth W of the input echo signal. The transmission control unit 5 stores these values, i.e., $f_P$, $f_H$, $f_L$, and W as flaw detection conditions in the flaw detection condition memory 6. The flow then advances to step P3.

When the echo signals b of all the channels except for the reference channel are to be matched with specific flaw detection conditions, the transmission control unit 5 reads out frequency characteristics such as the optimal peak frequency $f_P$ and the optimal frequency bandwidth W stored (P2) in the flaw detection condition memory 6.

In step P3, the transmission control unit 5 reads out the allowable ranges $\Delta fm$ and $\Delta Wm$ from the flaw detection condition memory 6 and sets them in, e.g., a buffer memory, thereby setting parameter control steps $\Delta f$ and $\Delta N$. The carrier frequency $f_c$ and the cycle count N of the ultrasonic transmission unit 3 are set to initial values.

In step P4, the transmission control unit 5 causes the ultrasonic transmission unit 3 to output the pulse signal a having the set carrier frequency $f_c$ and the set cycle count N to the ultrasonic probe 2. The ultrasonic receiving unit 4 receives an echo signal b from the ultrasonic probe 2. The signal analysis unit 7 performs frequency analysis of the echo signal b to obtain the peak frequency $f_P$ and the frequency bandwidth W. In step P5, the transmission control unit 5 compares the peak frequency $f_P$ of the echo signal b with the peak frequency $f_{Pa}$ as one of the preset flaw detection conditions. If the difference between the measured peak frequency $f_P$ and the peak frequency $f_{Pa}$ as the flaw detection condition does not fall within the allowable range $\Delta fm$ in step P6, the carrier frequency $f_c$ of the pulse signal a is changed by the small frequency $\Delta f$ in step P7. The flow then returns to step P4, and another pulse signal a is then output.

When the difference between the measured peak frequency $f_P$ and the measured peak frequency $f_P$ falls within the allowable range $\Delta fm$ in step P6, the transmission control unit 5 compares the measured frequency bandwidth W with the frequency bandwidth W as one of the flaw detection conditions in step P8. If the difference between the measured frequency bandwidth W and the frequency bandwidth W as one of the flaw detection conditions does not fall within the allowable range $\Delta Wm$ in step P9, the cycle count N of the pulse signal a is changed by the small cycle count $\Delta N$ in step P10. The flow then returns to step P4, and another pulse signal a is output.

When the difference between the measured frequency bandwidth W and the frequency bandwidth W as the flaw detection condition falls within the allowable range $\Delta Wm$ in step P9, flaw detection condition setup processing for this channel is completed.

Figure 4:
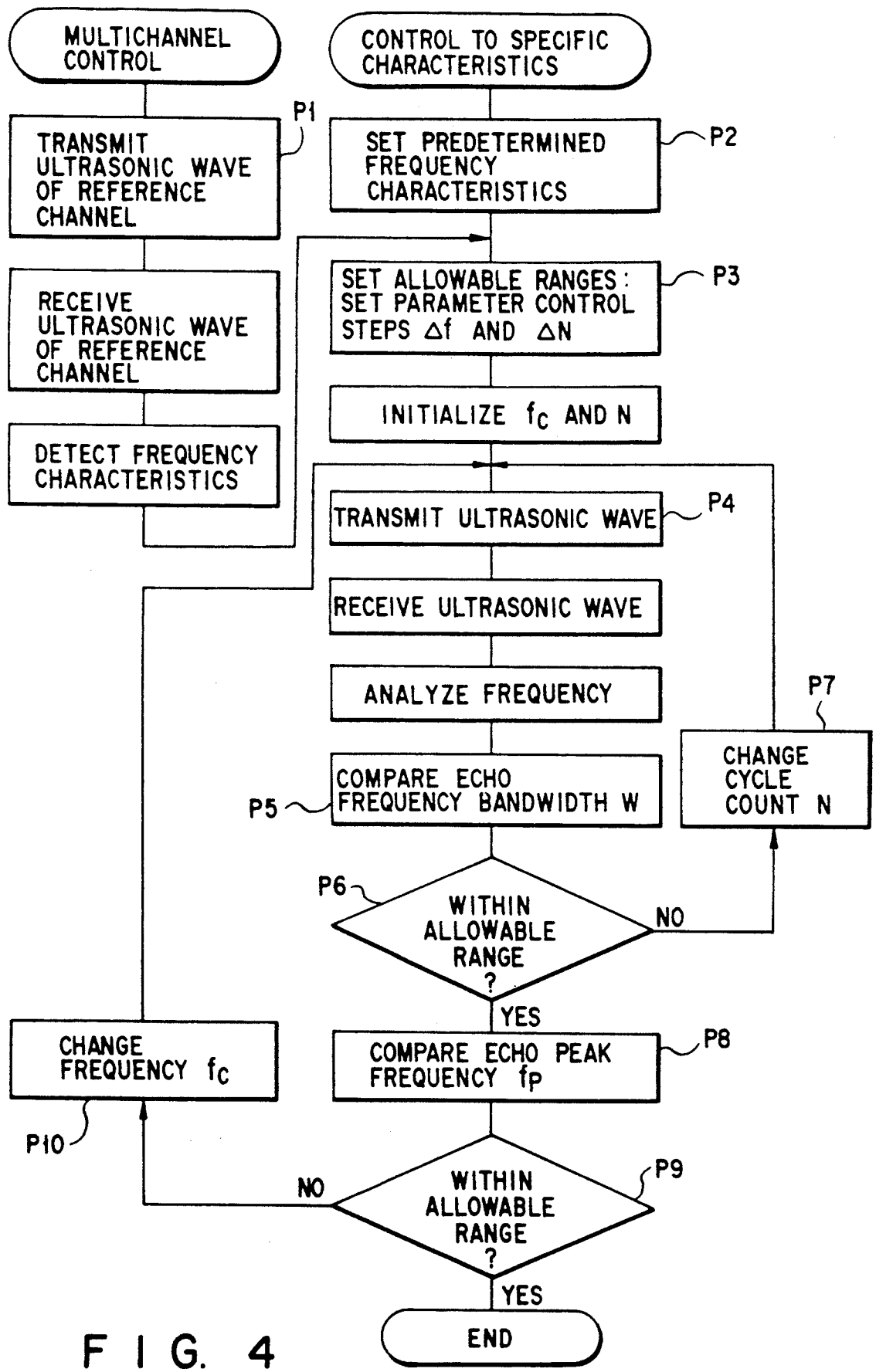
FIG. 4 is a flow chart showing an operation of an ultrasonic flaw detection apparatus according to another embodiment of the present invention.

As shown in FIG. 4, setup processing of the frequency bandwidth W may be performed before setup processing of the peak frequency $f_P$.

Effects of the ultrasonic flaw detection apparatus having the above arrangement will be described with reference to FIGS. 5A to 6B.

Figure 5A:
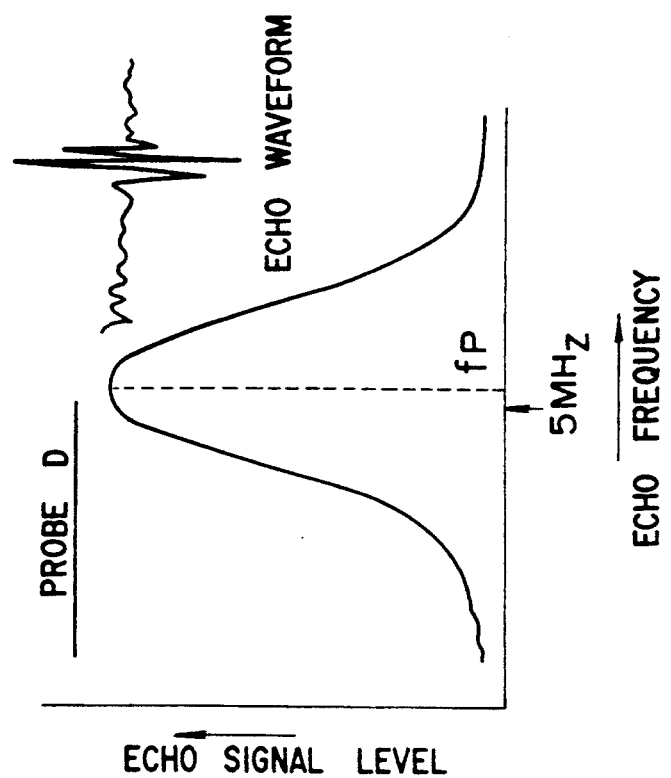
FIGS. 5A and 5B are graphs each showing an echo signal waveform and a frequency characteristic curve which are measured by a conventional method.
Figure 5B:
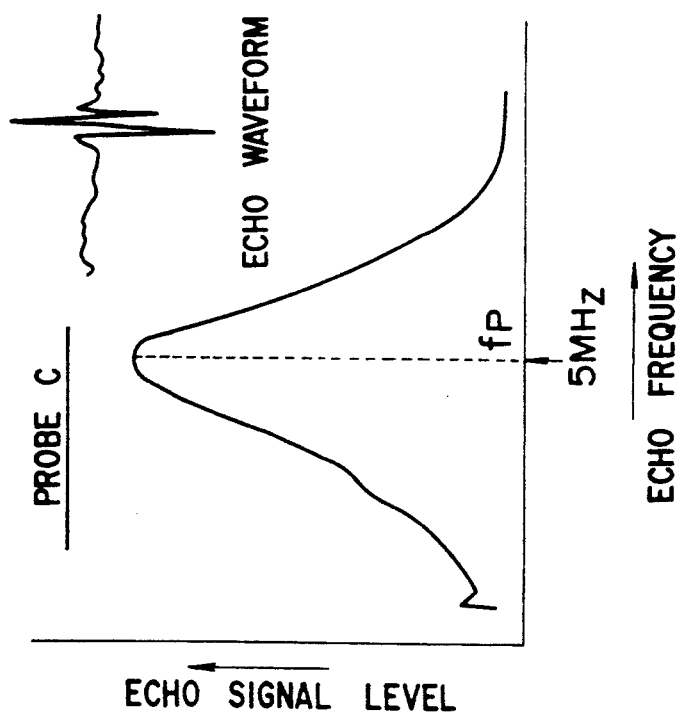

FIGS. 5A and 5B are graphs showing signal waveforms and frequency characteristics of echo signals b obtained by flaw detection using two ultrasonic probes C and D having identical technical specifications. The ultrasonic probes C and D are driven such that the same impulse signal as in the conventional apparatus is applied to the object 1 having a reference defect or flaw. As shown in FIGS. 5A and 5B, even if these ultrasonic probes have the identical specifications, a difference occurs between the resultant echo signals b. Peak frequencies $f_P$ are different from each other between the echo signals by about 0.5 MHz, and their frequency bandwidths W are also slightly different from each other.

Figures 6A, 6B:
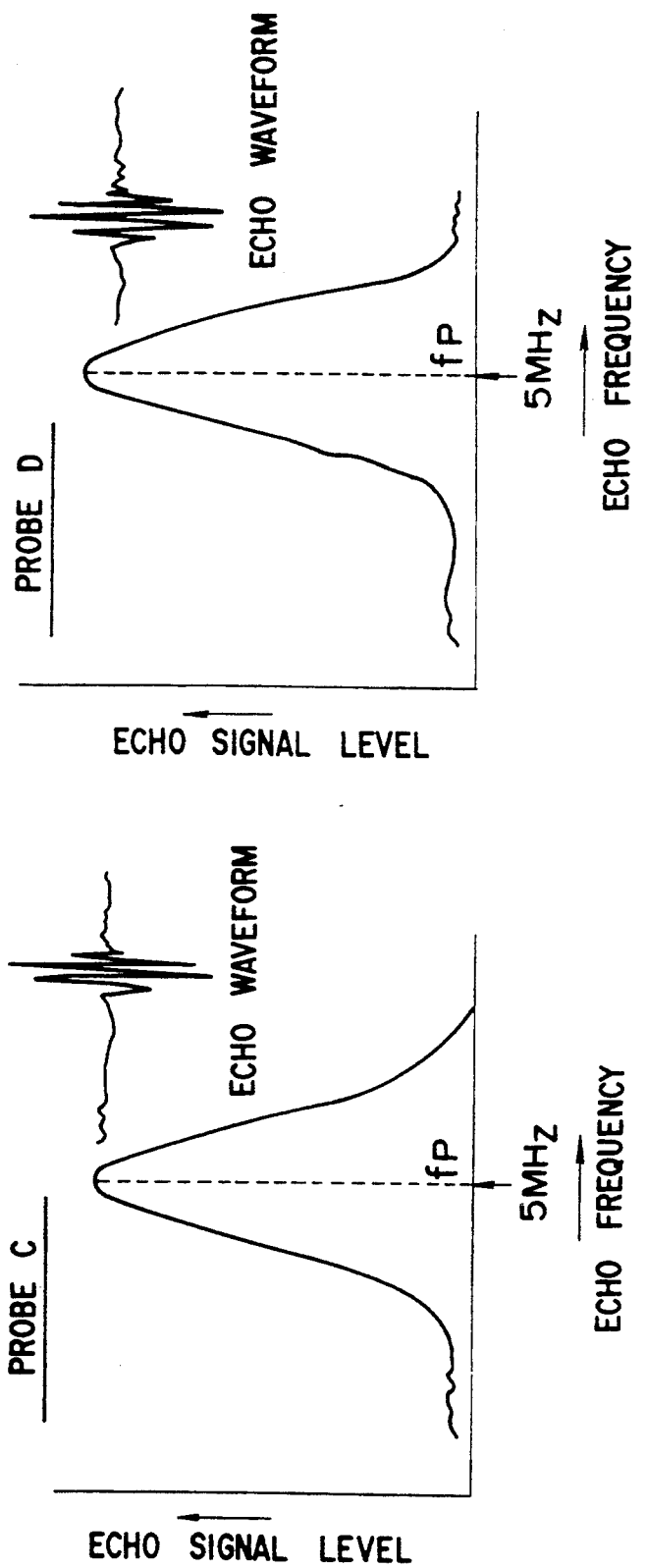
FIGS. 6A and 6B are graphs each showing an echo signal waveform and a frequency characteristic curve which are measured by the method of the embodiment.

FIGS. 6A and 6B are graphs showing signal waveforms and frequency characteristics of echo signals b obtained when flaw detection is performed using the above two ultrasonic probes C and D. The carrier frequencies $f_c$ and the cycle counts N of the pulse signals a are set by control as shown in FIG. 3 so that the peak frequencies $f_P$ and the frequency bandwidths W of the resultant echo signals b coincide with each other. As is understood from FIGS. 6A and 6B, even if a characteristic difference is present between the ultrasonic probes C and D, the flaw detection conditions represented by the peak frequencies $f_P$ and the frequency bandwidths W of the output echo signals b can coincide with each other. That is, flaw detection errors between the channels in the multichannel ultrasonic flaw apparatus can be minimized.

Figure 7:
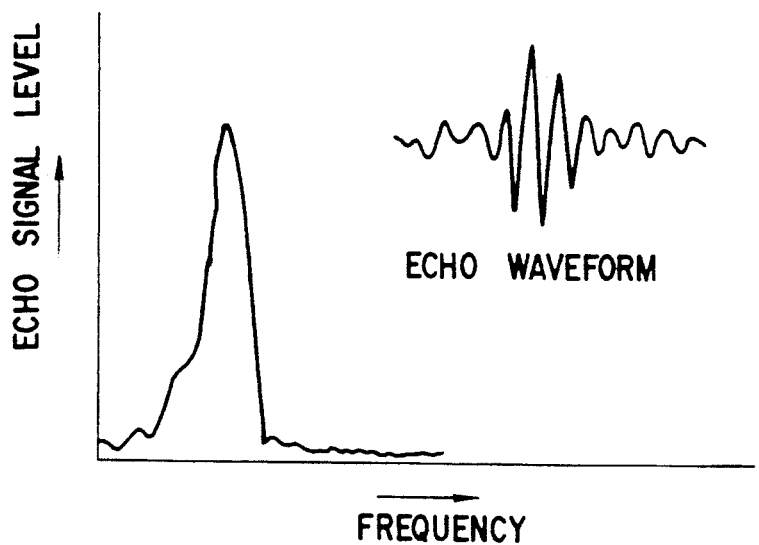
FIG. 7 is a graph showing an echo signal waveform representing a sample defect and a frequency characteristic curve which are measured by the method of the embodiment.
Figure 8:
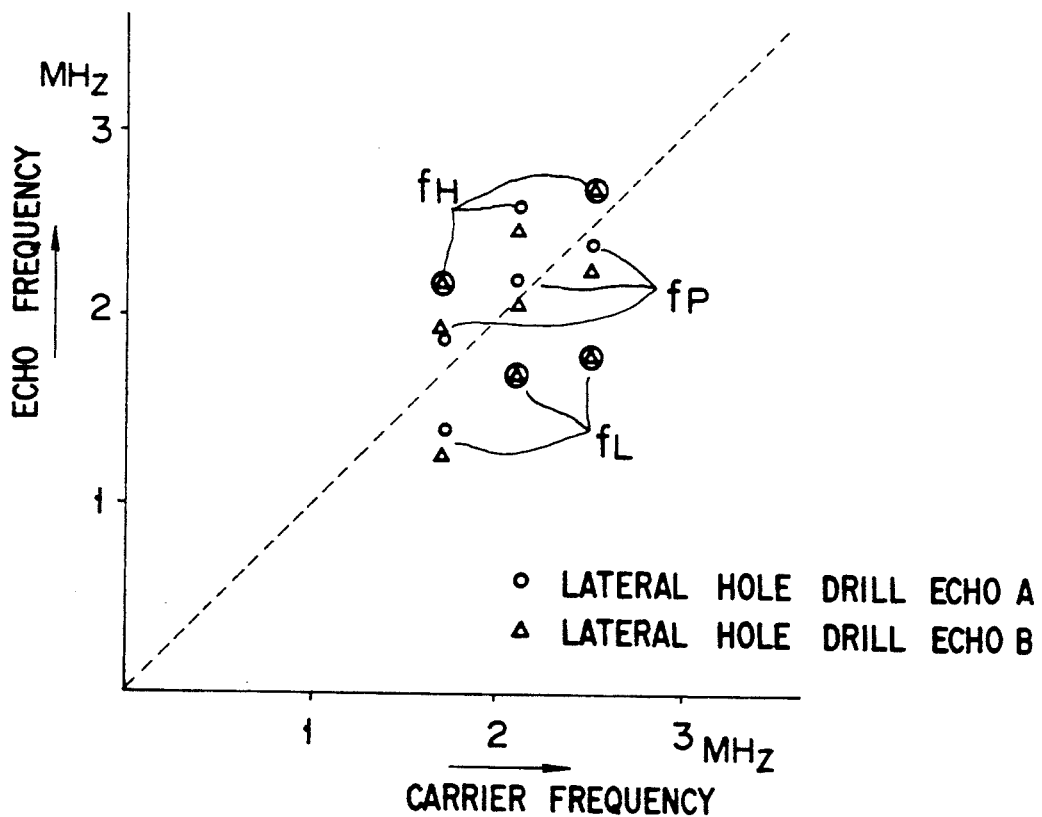
FIG. 8 is a graph showing a relationship between the carrier frequency and echo frequency which are measured by the method of the embodiment.
Figure 11A:
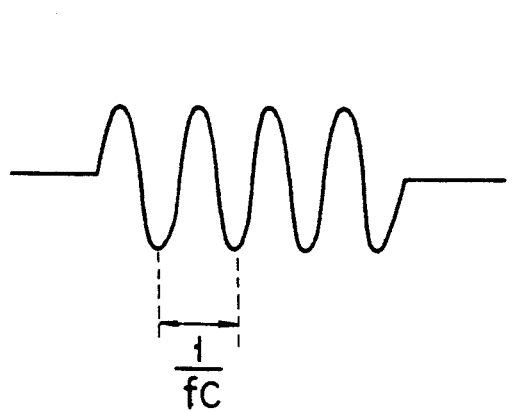
FIG. 11A is a waveform chart showing a tone-burst pulse signal.
Figure 11B:
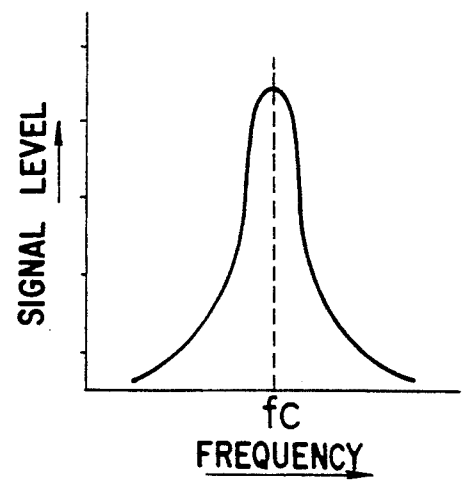
FIG. 11B is a graph showing a frequency characteristic curve of the pulse signal shown in FIG. 11A.
Figure 12:
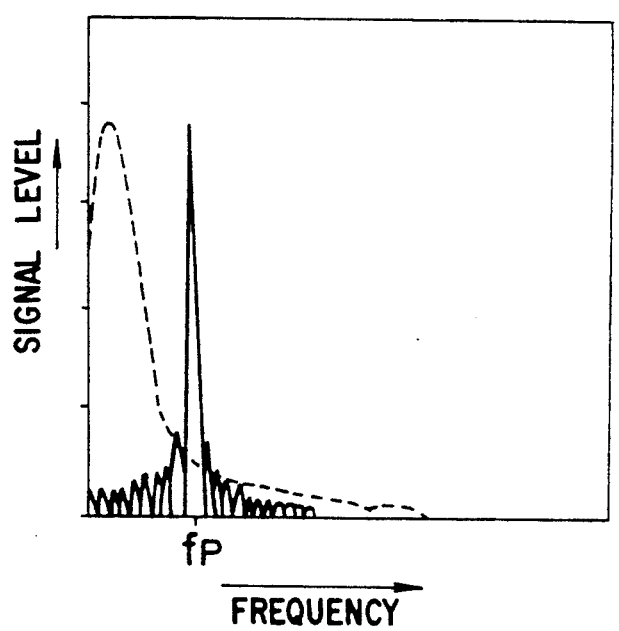
FIG. 12 is a graph showing frequency characteristic curves of echo signals of the tone-burst pulse signal and an impulse signal.
Figure 13:
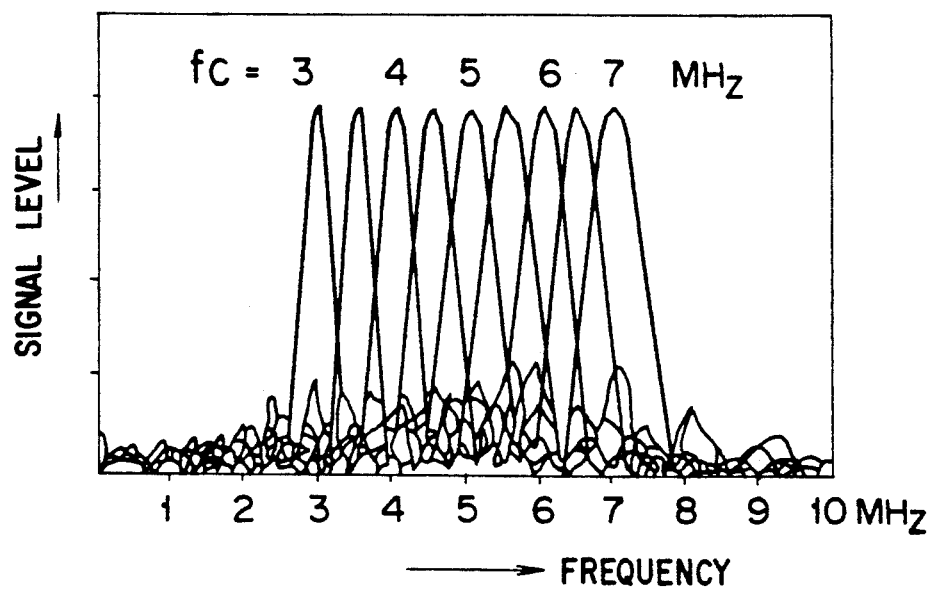
FIG. 13 is a graph showing a relationship between the carrier frequency of the tone-burst pulse signal and the peak frequency of the echo signal.
Figure 14A:
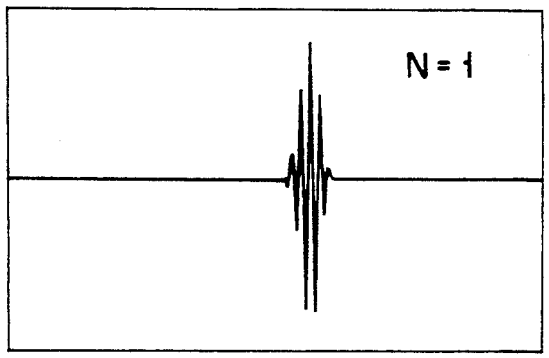
FIGS. 14A and 14B are graphs showing a relationship between the pulse signal waveform and the frequency characteristics when the cycle count of the tone-burst pulse signal cycle count is 1.
Figure 14B:
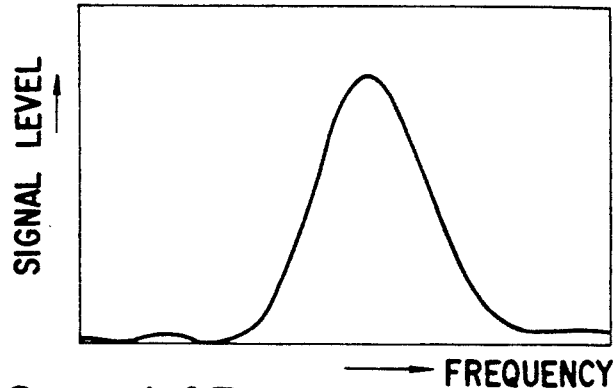
Figure 15B:
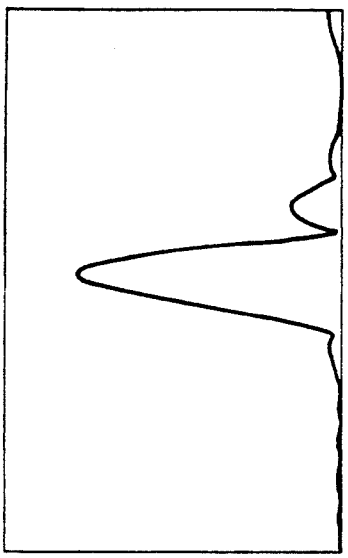
FIGS. 15A and 15B are graphs showing a relationship between the pulse signal waveform and the frequency characteristics when the cycle count of the tone-burst pulse signal cycle count is 5.
Figure 16B:
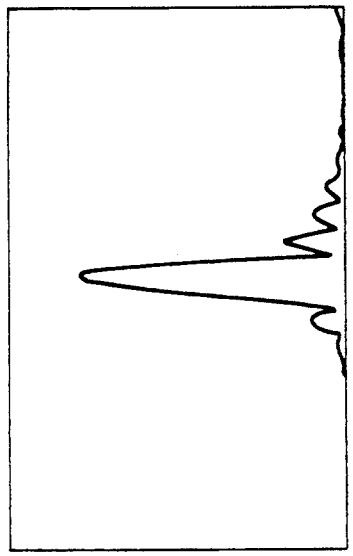
FIGS. 16A and 16B are graphs showing a relationship between the pulse signal waveform and the frequency characteristics when the cycle count of the tone-burst pulse signal cycle count is 10.
Figure 15A:
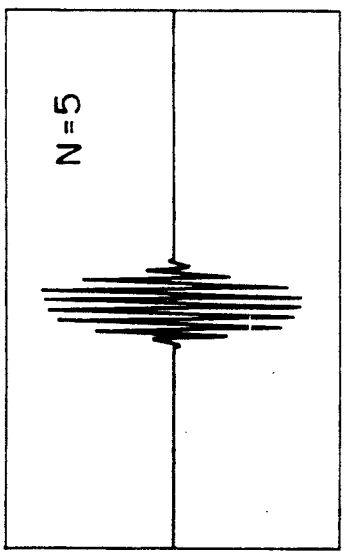
Figure 16A:
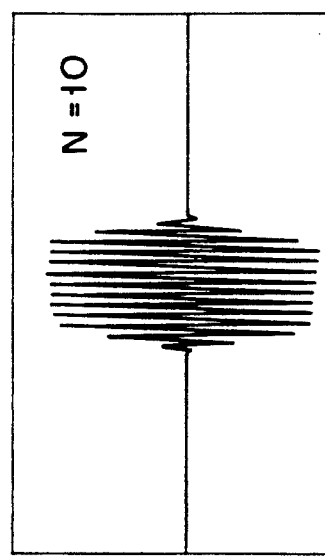

FIGS. 7 and 8 are graphs obtained when flaw detection is performed after two different lateral test holes A and B are formed. An object 1 comprises a high attenuation material in which correlation between the lateral hole diameter and the signal level of an echo signal is lost. The ultrasonic flaw detection method of the above embodiment is applied to this object 1. As shown in FIG. 7, an echo signal b obtained upon detection of the lateral hole can maintain a single frequency.

That is, an optimal peak frequency $f_P$ of the echo signal is set to be an optimal value determined by the material of this object 1, and its frequency bandwidth W is set narrow, thereby minimizing noise echoes, caused by the structure of the object 1, included in the echo signal b. The S/N ratio of the echo signal b can be largely increased, and flaw detection precision can be greatly improved.

There is often an object having flaw detection characteristics which make it difficult to detect a defect due to a low S/N ratio caused by high attenuation (caused by ultrasonic scattering) and drill echoes. This object has a small frequency difference between the peak frequency $f_P$ of the echo signal output by a wave reflected by a defect and the peak frequency of the echo signal of structural noise such as drill echoes caused by the composition of the material structure of the object 1.

The tone-burst pulse signal b is used to adjust the carrier frequency $f_c$ of the pulse signal b to slightly shift the peak frequency $f_P$ of the echo signal obtained upon detection of a defect from the peak frequency of the echo signal of the structural noise. At the same time, the cycle count N is adjusted to be an appropriate value, and the frequency bandwidth W of the echo signal b is set to be minimized. In principle, then, the S/N ratio of the echo signal b output from the ultrasonic probe 2 can be greatly improved as compared with the conventional technique using the impulse signal.

As shown in FIG. 8, even if the carrier frequency $f_c$ of the pulse signal a is changed, the peak frequency $f_P$ and the $-6$-dB lower frequencies $f_H$ and $f_L$ have the same tendency as the experimental results shown in FIGS. 9A and 10A. Even if the object comprises a high attenuation material, the peak frequency $f_P$ and the frequency bandwidth W of the echo signal b can be independently controlled. Therefore, control is not complicated, and the setup operations of the ultrasonic flaw detection conditions can be facilitated.

The present invention has been applied to the method and apparatus for performing ultrasonic flaw detection to detect a defect or flaw present in an object. However, the principle of the present invention is applicable to a wide range of flaw detection. For example, the present invention is applicable to an ultrasonic tester, an ultrasonic flaw detection unit, and an ultrasonic diagnosis apparatus, all of which use a pulse echo method.

When adjustment and uniform control in the frequency range of transmission pulses applied to objects are established, the present invention is also applicable to the following regions:

(a) Flaw discrimination by frequency optimization for a boundary damage of various types of bonding materials and coating materials, or damage evaluation in a frequency range; and (b) Applications to evaluation of material properties by means of pulse propagation behavior analysis in consideration of information of the frequency region.

What is claimed is:

1. A method of performing ultrasonic flaw detection, comprising the steps of:
   outputting a pulse signal having a carrier frequency and a cycle count, both of which are designated, to an ultrasonic probe attached to an object to be tested and causing an ultrasonic wave to be incident on the object;
   causing said ultrasonic probe to receive a reflected wave of the ultrasonic wave incident on the object to obtain an echo signal;
   changing the carrier frequency of the pulse signal so that a peak frequency of the received echo signal becomes a predetermined frequency;
   changing the cycle count of the pulse signal so that a frequency bandwidth of the received echo signal becomes a predetermined bandwidth; and
   detecting a defect present in the object in accordance with the echo signal output from said ultrasonic probe.

2. A method of performing ultrasonic flaw detection, comprising the steps of:
   outputting a pulse signal having a carrier frequency and a cycle count, both of which are designated, to an ultrasonic probe attached to an object to be tested and causing an ultrasonic wave to be incident on the object;
   causing said ultrasonic probe to receive a reflected wave of the ultrasonic wave incident on the object to obtain an echo signal;
   changing the cycle count of the pulse signal so that a frequency bandwidth of the received echo signal becomes a predetermined bandwidth;
   changing the carrier frequency of the pulse signal so that a peak frequency of the received echo signal becomes a predetermined frequency; and
   detecting a defect present in the object in accordance with the echo signal output from said ultrasonic probe.

3. A method of performing ultrasonic flaw detection, comprising the steps of:
   outputting a pulse signal having a carrier frequency and a cycle count, both of which are designated, to an ultrasonic probe attached to an object to be tested and causing an ultrasonic wave to be incident on the object;
   causing said ultrasonic probe to receive a reflected wave of the ultrasonic wave incident on the object to obtain an echo signal;
   changing the carrier frequency of the pulse signal independently of a frequency bandwidth of the echo signal so that a peak frequency of the echo signal becomes a predetermined frequency;
   changing the cycle count of the pulse signal independently of the peak frequency of the echo signal so that the frequency bandwidth of the echo signal becomes a predetermined bandwidth; and
   detecting a defect present in the object in accordance with the echo signal output from said ultrasonic probe.

4. A method according to claim 3, wherein the step of changing the carrier frequency of the pulse signal and the step of changing the cycle count of the pulse signal are repeated at least once each.

5. An apparatus for performing ultrasonic flaw detection, comprising:
   ultrasonic transmitting means for outputting a pulse signal having a designated carrier frequency and a designated cycle count,
   ultrasonic probe means, attached to an object to be tested, for outputting an ultrasonic wave to the object in response to the pulse signal input from said ultrasonic transmitting means and for outputting an echo signal,
   ultrasonic receiving means for receiving the echo signal output from said ultrasonic probe means,
   signal analyzing means for detecting a peak frequency and a frequency bandwidth of the echo signal received by said ultrasonic receiving means, and
   transmission control means for designating the carrier frequency and the cycle count of the pulse signal output from said ultrasonic transmitting means so that the detected peak frequency and the detected frequency bandwidth become a predetermined peak frequency and a predetermined frequency bandwidth, respectively.

6. An apparatus according to claim 5, further comprising flaw detection condition memory means for storing an optimal peak frequency and an optimal frequency bandwidth of materials of the object.

7. An apparatus according to claim 6, wherein
said flaw detection condition memory means stores the optimal peak frequency and the optimal frequency bandwidth of materials of the object, and allowable ranges of the optimal peak frequency and the optimal frequency bandwidth, and
said transmission control means designates to change the carrier frequency and the cycle count of the pulse signal when the peak frequency and the frequency bandwidth of the echo signal fall outside the allowable ranges.

8. An apparatus according to claim 6, wherein said signal analyzing means incorporates a fast Fourier transform circuit means for performing frequency analysis of the echo signal and calculates the peak frequency and the frequency bandwidth of the echo signal by using said fast Fourier transform circuit means.

9. An apparatus for performing ultrasonic flaw detection, comprising:
ultrasonic transmitting means for outputting a pulse signal having a designated carrier frequency and a designated cycle count,
ultrasonic probe means, attached through an ultrasonic wave propagation medium to an object to be tested, for outputting an ultrasonic wave to the object in response to the pulse signal input from said ultrasonic transmitting means and for outputting an echo signal,
ultrasonic receiving means for receiving the echo signal output from said ultrasonic probe means,
signal analyzing means for detecting a peak frequency and a frequency bandwidth of the echo signal received by said ultrasonic receiving means,
flaw detection condition memory means for storing a flaw detection condition peak frequency and a flaw detection condition frequency bandwidth of the echo signal, and
transmission control means for designating the carrier frequency and the cycle count of the pulse signal output from said ultrasonic transmitting means so that the detected peak frequency and the detected frequency bandwidth become the stored flaw detection condition peak frequency and the stored flaw detection condition frequency bandwidth, respectively.

10. An apparatus according to claim 9, further comprising display means for displaying the detected peak frequency and the detected frequency bandwidth of the echo signal.

11. An apparatus according to claim 9, wherein said signal analyzing means incorporates a fast Fourier transform circuit means for performing frequency analysis of the echo signal and calculates the peak frequency and the frequency bandwidth of the echo signal by using said fast Fourier transform circuit means.

12. An apparatus according to claim 11, further comprising display means for determining a level of the echo signal, determining the presence/absence of a defect, calculating a size of the defect, and displaying the size of the defect.

* * * * *